(12) United States Patent
Matsumoto

(10) Patent No.: US 7,289,201 B2
(45) Date of Patent: Oct. 30, 2007

(54) INSPECTION DEVICE FOR TRANSPARENT SUBSTRATE END SURFACE AND INSPECTION METHOD THEREFOR

(75) Inventor: Junichi Matsumoto, Sakai (JP)

(73) Assignee: Mitsuboshi Diamond Industrial Co., Ltd., Suita (JP)

( * ) Notice: Subject to any disclaimer, the term of this patent is extended or adjusted under 35 U.S.C. 154(b) by 0 days.

(21) Appl. No.: 10/547,827

(22) PCT Filed: Mar. 3, 2004

(86) PCT No.: PCT/JP2004/002668

§ 371 (c)(1),
(2), (4) Date: Sep. 2, 2005

(87) PCT Pub. No.: WO2004/079352

PCT Pub. Date: Sep. 16, 2004

(65) Prior Publication Data

US 2006/0221333 A1    Oct. 5, 2006

(30) Foreign Application Priority Data

Mar. 4, 2003 (JP) ............................. 2003-057840

(51) Int. Cl.
*G01N 21/00* (2006.01)
(52) U.S. Cl. ................................. 356/239.1
(58) Field of Classification Search .. 356/237.1–237.5, 356/239.1–239.8; 250/559.45
See application file for complete search history.

(56) References Cited

U.S. PATENT DOCUMENTS 3,985,454 A * 10/1976 Fletcher et al. .......... 356/239.1
6,294,793 B1 * 9/2001 Brunfeld et al. ........ 250/559.45
6,618,136 B1 * 9/2003 Ishida ..................... 356/239.1

FOREIGN PATENT DOCUMENTS

| JP | 06-258231 | 9/1994 |
|----|-----------|--------|
| JP | 10-132758 | 5/1998 |
| JP | 10-213551 | 8/1998 |
| JP | 2002-214157 | 7/2002 |
| JP | 2003-247953 | 9/2003 |
| JP | 2003-270170 | 9/2003 |

* cited by examiner

*Primary Examiner*—Hoa Q. Pham
(74) *Attorney, Agent, or Firm*—Renner, Otto, Boisselle & Sklar, LLP

(57) ABSTRACT

An inspection apparatus for inspecting an end face of a transparent substrate and an inspection method for inspecting an end face of a transparent substrate according to the present invention are capable of reliably and accurately detecting defects at the end face of the transparent substrate. When a display panel substrate 10 which is a transparent substrate to placed on a rotating table 21, a light is intermittently emitted from an end-face illuminating unit 39 arranged opposite to the end face of the display panel substrate 10. The light emitted along the surface of the substrate 10 is reflected from a lower reflecting mirror 42 toward the end face of the transparent substrate 10. The end face and an adjacent portion thereof are imaged by a CCD camera 36. Defects at the end face of the display panel substrate 10 are detected based on an image density of each pixel in the obtained image data.

30 Claims, 13 Drawing Sheets

FIG.6
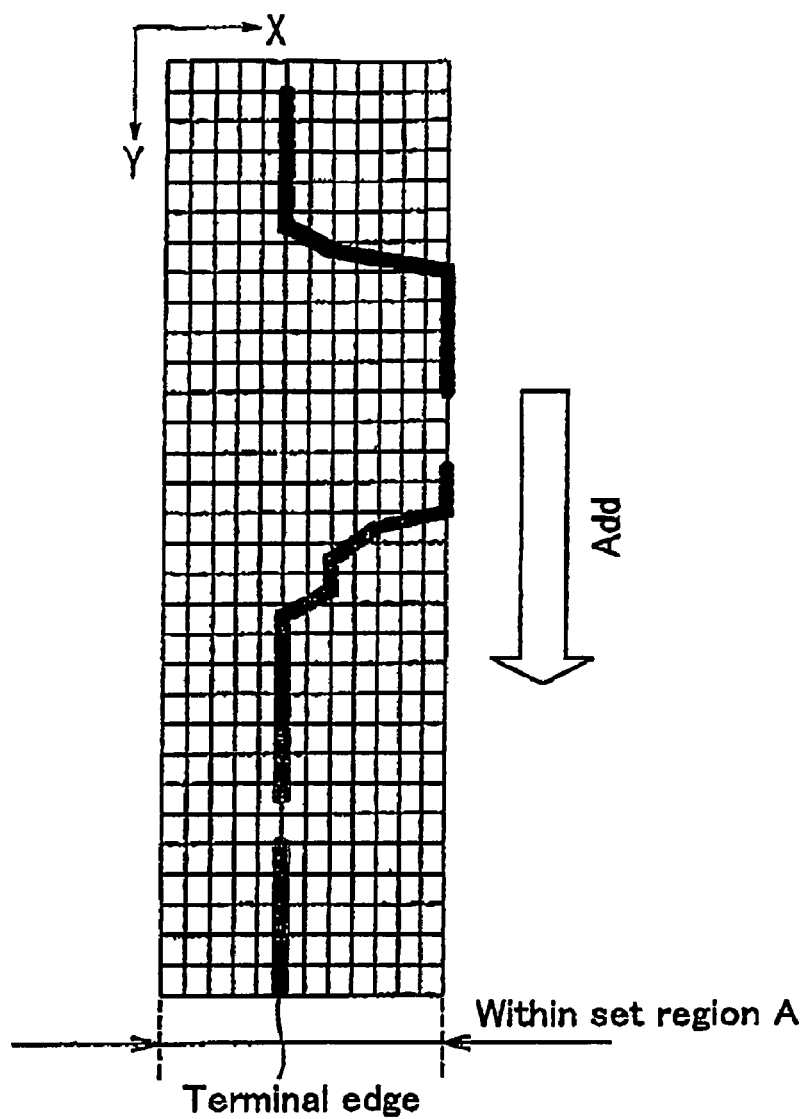
(a)
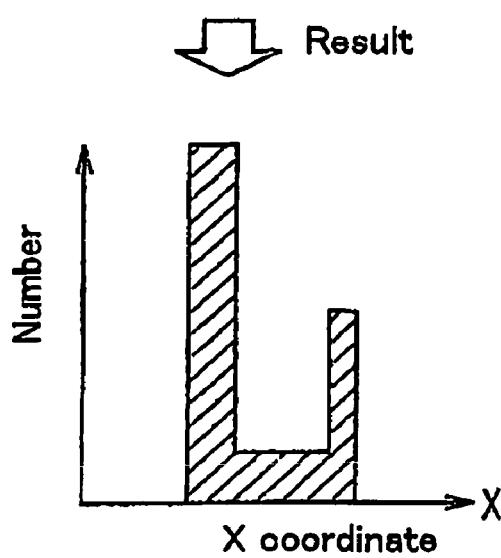
(b)

FIG.7
(a)
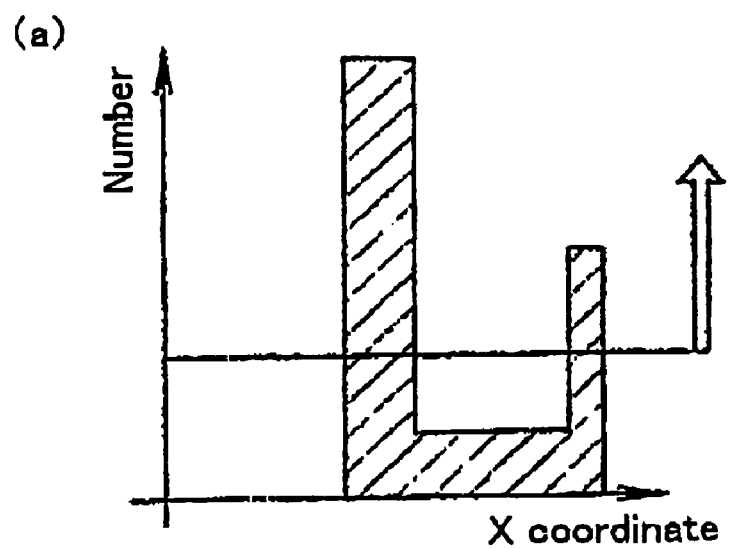
(b)
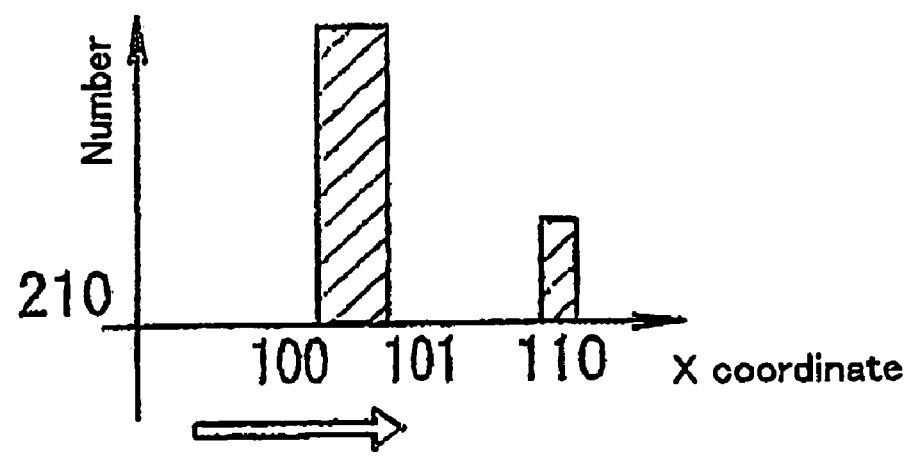

FIG.10
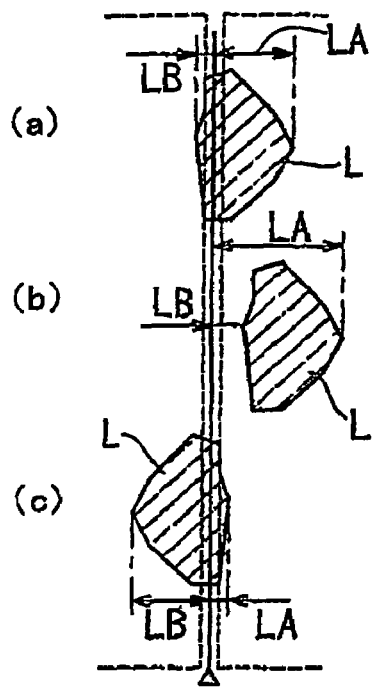
FIG.11
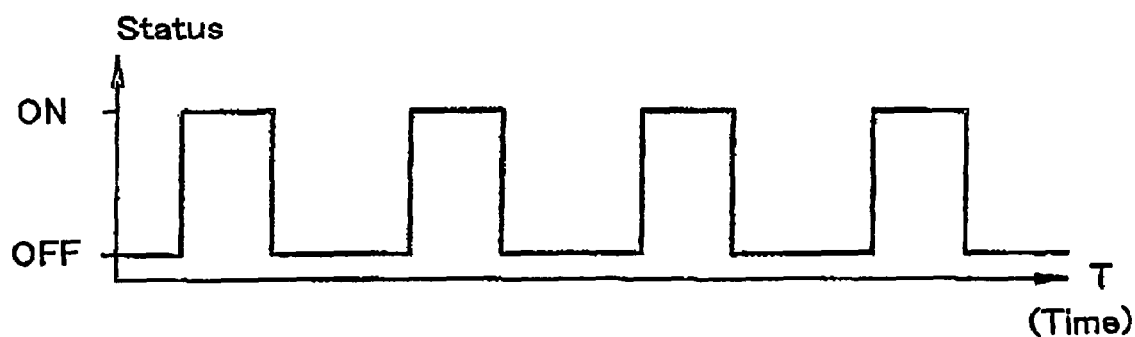
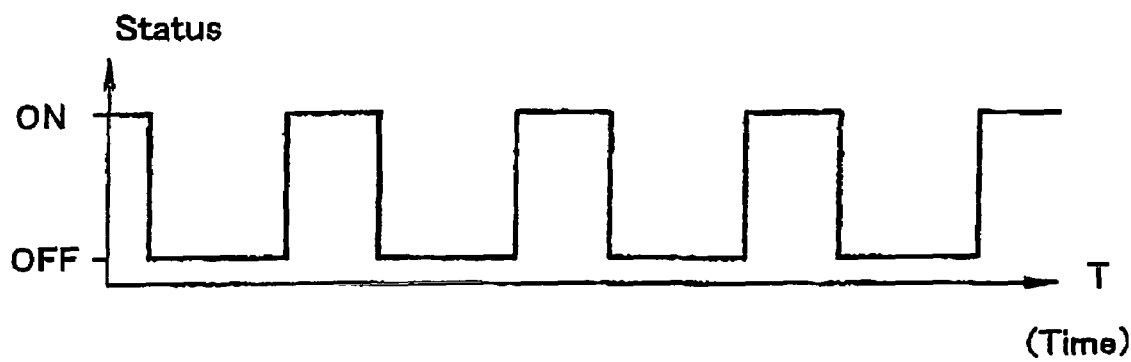

INSPECTION DEVICE FOR TRANSPARENT SUBSTRATE END SURFACE AND INSPECTION METHOD THEREFOR

The present invention relates to an apparatus and method for inspecting any defects at an end face of a transparent substrate, including a transparent glass substrate, that is cut into a predetermined size. In the transparent substrate, a bonded substrate made up of a pair of glass substrates bonded and used for flat display panels is also included.

BACKGROUND ART

Liquid crystal display (LCD) panel substrates used in LCD apparatuses are formed by filling a gap between a pair of glass substrates with liquid crystals. A wiring line, a thin-film transistor (TFT) and the like are provided on one glass substrate, which is generally referred to as a TFT substrate. A color filter (CF) is provided on the other glass substrate, which is generally referred to as a CF substrate. Such a display panel substrate is, for example, formed by bonding a pair of mother glass substrates together and then cutting it into the size of the display panel substrate. A predetermined TFT, a wiring line and the like are provided in advance on the mother glass substrate to be formed into the TFT substrate.

FIG. 13 is a schematic perspective view of a cut display panel substrate. A TFT, a wiring line and the like are provided on a TFT substrate 11 (arranged in the lower part in FIG. 13) partially forming a display panel substrate 10. On one side of the TFT substrate 11, a terminal section 11a on which a plurality of terminals 11b are provided to be respectively connected to each wiring line is formed. A CF substrate 12 completing the formation of the display panel substrate 10 and the TFT substrate 11 are bonded with a predetermined gap to be filled with liquid crystals therebetween such that the terminal section 11a is exposed.

In the case of manufacturing the display panel substrate 10 having the structure described above, as shown in FIG. 14(a), the terminals 11b of the terminal section 11a provided on a TFT substrate 11A of a bonded glass substrate 10A are electrically connected to each other with a short link 11c provided on a side edge of the terminal section 11a of the TFT substrate 11A. The short link 11c prevents the accumulation of charge in each of the terminals 11b and the wiring lines and protects the wiring lines from electrostatic damage. After a plurality of bonded glass substrates 10A are cut from a bonded mother glass substrate for which a mother CF substrate and a mother TFT substrate are bonded, the TFT substrate 11A is cut along a cutting line 11d shown in FIG. 14(b), thus disengaging the connection of the terminals to each other 11b with the short link 11e (see FIG. 13). When the TFT substrate 11A is cut along the cutting line 11d, then the end face 11e extending along the cutting line 11d is ground and the both edges of the end face 11e are subjected to chamfering. In this case, in addition to the end face 11e along the terminal section 11a of the TFT substrate 11, at an end face where the terminal section of the display panel substrate 10 is not formed, the top edge of the CF substrate 12 and the bottom edge of the TFT substrate 11 are subjected to chamfering.

Each of the bonded glass substrates 10A is formed to respectively out a pair of bonded mother glass substrates. FIG. 15 shows a section view of the bonded glass substrate 10A cut from the bonded mother substrate. In this case, since a CF substrate 12A is cut so that the terminal section 11a provided on the TFT substrate 11A is exposed, the position of cutting the CF substrate 12A is different from the position of cutting the TFT substrate 11A. As shown in FIG. 15, the position of cutting the CF substrate 12A is adjacent to a sealing member 13 provided for bonding the TFT substrate 11A and the CP substrate 12A to each other. Therefore, while the CF substrate 12A is cut, the tension of the sealing member 13 is applied to an end face 12e of the CF substrate 12A to be cut, and as a result, the end face 12e to be cut may be gradually inclined (i.e., by hollowing out) toward the direction that approaches to the sealing member 13 as the end face 12e approaches to the sealing member 13, as indicated by dashed lines in FIG. 15.

In the case when the bonded glass substrate 10A is cut from a pair of mother glass substrates bonded to each other and when the terminal section 11a of the TFT substrate 11A is cut to remove the short link 11c from the bonded glass substrate 10A, an end face of the TFT substrate 11 or an end face of the CF substrate 12 of the cut display panel substrate 10 may cause chipping. If a relatively-large shell-shaped chipping occurs on the end face 11e adjacent to the terminal section 11a of the TFT substrate 11, the chipping may extend toward the inside of the TFT substrate over time and thus the terminals 11b provided on the terminal section 11a may be broken.

As such, if the display panel substrate 10 that is cut from a pair of mother glass substrates bonded to each other and that has a defect, such as a chipping, in the end face of the TFT substrate 11 or in the end face the CF substrate 12 is transferred to the next step to be formed into a liquid crystal display apparatus, the manufactured liquid crystal display apparatus may not operate properly, i.e., a defective product may be produced.

If a defective product is found in the last stage of manufacturing liquid crystal display apparatuses, there is a problem that the manufacturing yield of liquid crystal display apparatuses is significantly reduced. In particular, as described above, in a case where the end face 12e of the CF substrate 12 has been inclined, moisture may penetrate the gap between the inclined end face 12e and the TFT substrate 11 in a subsequent cleansing step. Thus the terminals 11b of the terminal section 11a of the TFT substrate 11 may be subjected to corrosion due to the moisture, thereby increasing the possibility of product defects.

In order to solve such problems, it is preferable that defects, such as an inclination of the end face, a chipping the end face and the like, be detected by inspecting the end face of the TFT substrate 11 or the end face of the CF substrate 12 in the display panel substrate 10 cut from the bonded mother substrate before the display panel substrate 10 is transferred to the next step. However, it is difficult to efficiently and accurately detect defect parts, such as the inclination of the end face, the chipping of end face and the like, of the display panel substrate 10.

Moreover, for the end face of the TFT substrate 11 and the end face of the CF substrate 12 in the display panel substrate 10, after the gap between the TFT substrate 11 and the CF substrate 12 is filled with liquid crystals, each of the edges of the end faces is generally subjected to chamfering by wet grinding process with grind stones. However, it is difficult to check whether a predetermined amount of the edges of the end faces are reliably subjected to chamfering.

The present invention is to solve such problems. The object of thereof is to provide an inspection apparatus and an inspection method capable of efficiently and accurately detecting a defect, such as chipping, for inspecting an end face of a transparent substrate and also capable of readily, for example, inspecting the state of a part subjected to chamfering of the end face.

DISCLOSURE OF THE INVENTION

An inspection apparatus for inspecting an end face of a transparent substrate according to the present invention includes a table for supporting the transparent substrate; a first illuminating means arranged opposite to the end face of the transparent substrate placed on the table, the first illuminating means being for intermittently emitting a light to the end face; a imaging means arranged in at least one direction with respect to a surface of the transparent substrate, the end face and the surroundings thereof being an imaging region of the imaging means; and an image processing means for detecting a defect of the end face based on an image density of image data captured by the imaging means. Thereby, the objective described above is achieved.

The inspection apparatus may further include first reflecting means for reflecting the light emitted from the first illuminating means, wherein the imaging means is arranged so that the end face and the surroundings thereof are the imaging region illuminated with the light reflected from the first reflecting means.

The imaging means may be arranged opposite to the first reflecting means with respect to the transparent substrate.

The table may support the transparent substrate in a horizontal position. The first reflecting means may be provided below the transparent substrate.

The table may support the transparent substrate in a horizontal position. The second reflecting means may be provided above the transparent substrate.

The table may be movable in a horizontal direction.

The table may be rotatable about an axis vertical to a surface of the table.

The first reflecting means and the imaging means may be movable in an integral manner with respect to the table.

The first reflecting means may be integrally movable with respect to the first illuminating means.

In the first reflecting means, the direction of reflection with respect to the end face of the transparent substrate may be adjustable.

The second reflecting means and the imaging means may be movable in an integral manner with respect to the table.

The second reflecting means may be integrally movable with respect to the first illuminating means.

In the second reflecting means, the direction of reflection with respect to the end face of the transparent substrate may be adjustable.

The inspection apparatus may further include second illuminating means for intermittently emitting a light to the end face of the transparent substrate while the first illuminating means is off.

The first illuminating means may be a linear light source extending parallel to the end face of the transparent substrate.

The linear light source may be an LED array.

The imaging means may be a CCD camera.

The first illuminating means and the first reflecting means may be respectively provided on sides of the end faces at both side edges of the transparent substrate.

The first illuminating means and the second reflecting means may be respectively provided on sides of to the end faces at both side edges of the transparent substrate.

The image processing means may determine an image density of each pixel in image data captured by the imaging means and may identify the end face of the transparent substrate based on the image density of each pixel.

The image processing means may detect a defect based on the identified end face of the transparent substrate and the image density of each pixel.

An edge of the end face may be subjected to chamfering.

The image processing means may detect diffused reflection at the end face of the transparent substrate as a defective portion having a high intensity of light.

The transparent substrate may be a bonded glass substrate for which two glass substrates are bonded so that a terminal section is exposed, the two glass substrates having a predetermined gap to be filled with liquid crystals therebetween.

The image processing means is capable of switching an inspecting target between one of the end faces of a bonded glass substrate or both the end faces of the bonded glass substrate, the bonded glass substrate being bonded so that a terminal section is exposed.

An inspection method for inspecting an end face of a transparent substrate according to the present invention includes intermittently emitting a light to the end face of the transparent substrate by first illuminating means; imaging the end face and the surroundings thereof by imaging means; and detecting a defect of the end face based on an image density of image data captured by the imaging means. Thereby, the object described above is achieved.

In the emitting a light and the imaging step, the light intermittently emitted along the transparent substrate may be reflected from reflecting means toward the end face.

The end face may be intermittently illuminated with a light by second illuminating means while the first illuminating means for intermittently emitting a light to the end fade is off.

The detecting a defect may determine an image density of each pixel in image data captured by the imaging means, identify the end face of the transparent substrate based on the image density and detect a defect based on the identified end face of the transparent substrate and the image density of each pixel.

An edge of the end face may be subjected to chamfering.

The detecting a defect may detect diffused reflection at the end face of the transparent substrate as a defective portion having a high intensity of light.

The transparent substrate may be a bonded glass substrate for which two glass substrates are bonded so that a terminal section is exposed, the two glass substrates having a predetermined gap to be filled with liquid crystals therebetween.

The detecting a defect may be capable of switching an inspecting target between one of the end faces of a bonded glass substrate or both the end faces of the bonded glass substrate, the bonded glass substrate being bonded so that a terminal section it exposed.

BRIEF DESCRIPTION OF THE DRAWINGS

FIG. 6(a) is an illustration for explaining image processing in the inspection apparatus for inspecting an end face of a transparent substrate according to the present invention.

FIG. 6(b) is an illustration for explaining the image processing in the inspection apparatus for inspecting an end face of a transparent substrate according to the present invention.

FIG. 7(a) is an illustration for explaining the image processing in the inspection apparatus for inspecting an end face of a transparent substrate according to the present invention.

FIG. 7(b) is an illustration for explaining the image processing in the inspection apparatus for inspecting an end face of a transparent substrate according to the present invention.

FIG. 10 is an illustration for explaining the image processing in the inspection apparatus for inspecting an end face of a transparent substrate according to the present invention.

FIG. 11 is an illustration for explaining how an end-face illuminating unit and an epi-illuminating unit are turned on and off.

BEST MODE FOR CARRYING OUT THE INVENTION

Hereafter, embodiments of the present invention are described below.

Figure 1:
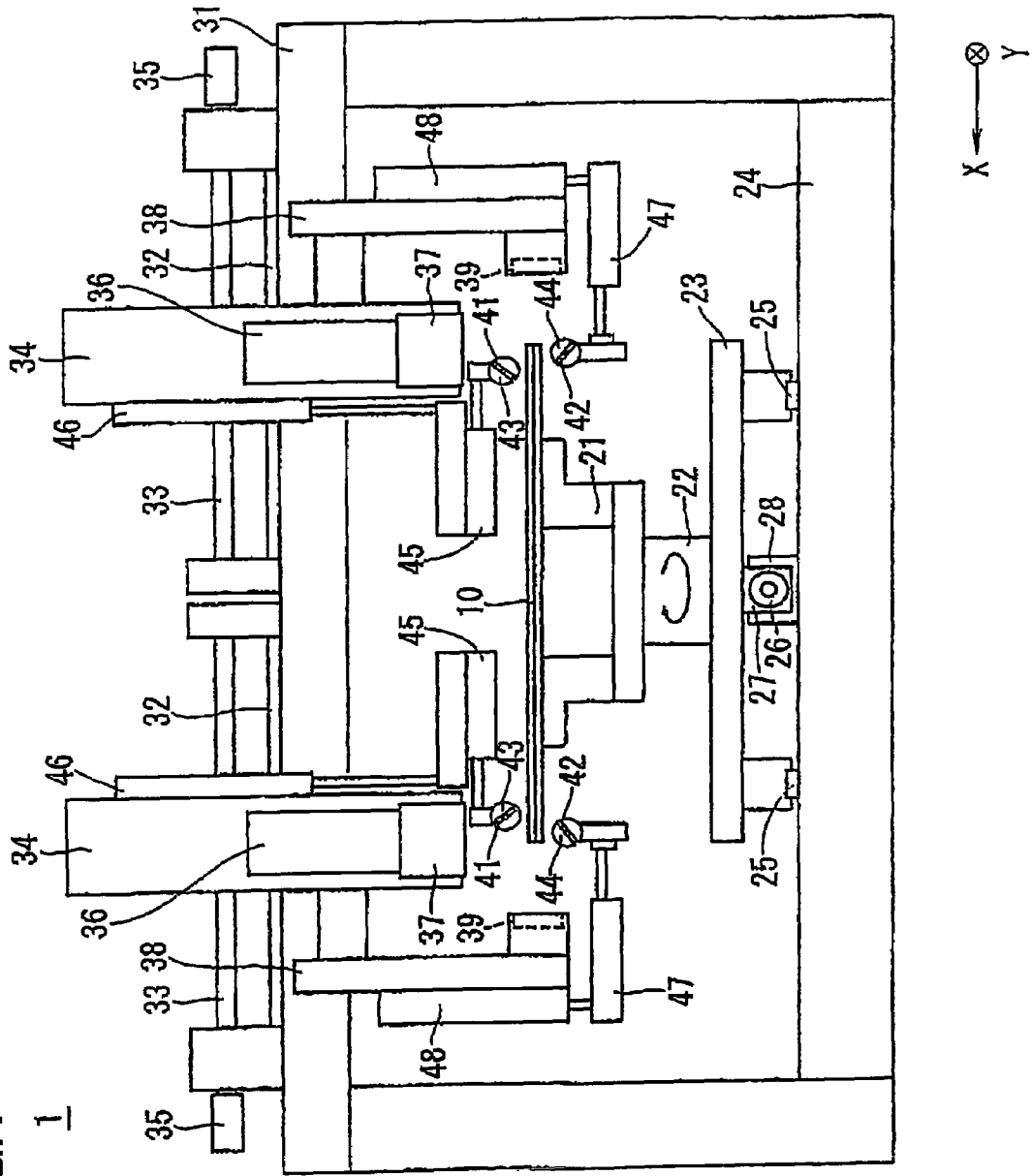
FIG. 1 is a schematic diagram showing the structure of an inspection apparatus for inspecting an end face of a transparent substrate according to an embodiment of the present invention.

FIG. 1 is a schematic diagram showing an example of an inspection apparatus for inspecting an end face of a transparent substrate according to the present invention. The inspection apparatus 1 for inspecting an end face of a transparent substrate is, for example, used for inspecting each end face of a TFT substrate 11 and a CF substrate 12 of a display panel substrate 10 shown in FIG. 13.

The inspection apparatus 1 for inspecting an end face of a transparent substrate includes a sliding table 23 provided above a base 24 so as to be slidable in a predetermined y-axis direction, a direct-drive (DD) motor 22 provided on the sliding table 23 and a rotating table 21 provided so as to be rotated by the DD motor 22. On the rotating table 21, the display panel substrate 10 is placed in a horizontal position.

The rotating table 21 vacuum-holds the placed display panel substrate 10 so that the display panel substrate 10 is fixed in a horizontal position. The DD motor 22 provided on the sliding table 23 has a rotating axis in a vertical direction. The rotating table 21 is rotated by the DD motor 22 around the vertical axis. The rotating table 21 is configured to support the display panel substrate 10 so that the periphery of the placed display panel substrate 10 is protruded into the outer circumference of the rotating table 21.

The sliding table 23 on which the DD motor 22 is provided is slidable along a pair of y-axis guide rails 25 which are provided on the base 24 in parallel to each other. A y-axis ball screw 26 in parallel with each y-axis guide rail is rotatably provided between the pair of y-axis guide rails 25. The y-axis ball screw 26 engages with a Y-axis ball nut 27 attached to the bottom face of the sliding table 23. A y-axis servomotor 28 is connected to one end of the y-axis ball screw 26 and rotates the y-axis ball screw 26 in forward and reverse directions. The sliding table 23 is slid along the pair of y-axis guide rails 25 in both directions (back and forth directions, which are vertical to the plane of FIG. 1) by the rotation of the y-axis ball screw 26 in the forward and reverse directions.

A support 31 is provided above the rotating table 21 on the base 24 so as to be bridged in a horizontal position along an x-axis direction, which is perpendicular to the y-axis ball screw 26 and each of the y-axis guide rails 25. A pair of y-axis guide rails 32 is provided on the support 31 along the direction perpendicular to the y-axis ball screw 26 and each of the y-axis guide rails 25 provided on the base 24 so that the pair of y-axis guide rails 32 is colinear. Sliding blocks 34 respectively engage with the x-axis guide rails 32 so as to be slidable.

X-axis ball screws 33 are bridged in a horizontal position above the support 31 parallel to each of the x-axis guide rails 32. The x-axis ball screws 33 respectively engage with x-axis ball nuts (not shown) attached to the sliding blocks 34. Optical system moving servomotors 35 are respectively connected to ends of the x-axis ball screws 33 located distant from each other. The optical system moving servomotors 35 respectively rotate the x-axis ball screws 33 in the forward and reverse directions. Therefore, the sliding blocks 34 are reciprocated in both x-axis directions (right and left directions in FIG. 1) along the x-axis direction by the rotation of the x-axis ball screws 33 in the forward and reverse directions.

The sliding blocks 34 protrude below the support 31 and lower ends of the sliding blocks 34 are adjacent to the display panel substrate 10 placed on the rotating table 21. Charge-coupled device (CCD) cameras 36 are respectively provided on the sliding blocks 34 with an optical axis in a vertical position. The CCD cameras 36 function to respectively image the end faces located at both sides of the TFT substrate 11 and the CF substrate 12, which constitute the display panel substrate 10 placed on the rotating table 21.

The imaging region of each of the CCD cameras 36 is a range of about 15 mm with respect to the optical axis so that each of the CCD cameras 36 can image each of an end face 11e of the terminal section 11a in the TFT substrate 11 and an end face 12e of the CP substrate 12 of the display panel substrate 10. Image data captured by the CCD cameras 36 is supplied to an image processing device 51 (see FIG. 2) and then is subjected to predetermined image processing.

Epi-illuminating units 37 used when side edges at both sides of the display panel substrate 10 are respectively aligned with respect to a region to be captured by the CCD cameras 36 with the optical axes of the epi-illuminating units 37 matched with the optical axle of the CCD cameras 36 in vertical position are arranged.

Connection blocks 38 extending along the vertical direction are respectively attached to the sliding blocks 34 such that one of the connection blocks 38 is connected to one side of one of the sliding block 34, the side being more distant than the other side of the other sliding block 34. End-face illuminating units 39 for respectively illuminating the end faces located on the both sides of the display panel substrate 10 placed on the rotating table 21 are respectively provided at the lower ends of the connection blocks 38 so as to oppose the corresponding and face.

Each of the end-face illuminating units 39 is, for example, made up of a linear light source extending along the horizontal direction. In this embodiment, each of the end-face illuminating units 39 is made up of a light-emitting diode (LED) array in which a plurality of LEDs are arranged in a horizontal direction.

Upper reflecting mirrors 41 for reflecting light emitted from the end-face illuminating units 39 toward the end faces located below the upper reflecting mirrors 41 are provided in a region above the side edges at the both sides of the display panel substrate 10 placed on the rotating table 21. Each of the upper reflecting mirrors 41 is, for example, respectively arranged at a distance of about 10 mm to 60 mm from the optical axis in a vertical position of each of the CCD cameras 36.

Lower reflecting mirrors 42 for reflecting light emitted from the end-face illuminating units 39 toward the end faces located above the lower reflecting mirrors 42 are provided in a region below the end faces. Each of lower reflecting mirrors 42 is, for example, respectively arranged at a distance of about 5 mm to 30 mm from the optical axis in a vertical position of each of the CCD cameras 36 and at a distance of about 5 mm to 25 mm from the top face of the display panel substrate 10.

The upper reflecting mirrors 41 function to reflect light emitted from the end-face illuminating units 39 and thus illuminate the end faces of the display panel substrate 10 located below the upper reflecting mirrors 41. In the same way, the lower reflecting mirrors 42 function to reflect light emitted from the end-face illuminating units 39 and thus illuminate the end faces of the display panel substrate 10 located above the lower reflecting mirrors 42. Each of the upper reflecting mirrors 41 has a length of 30 mm along the inclination direction in an inclined state shown in FIG. 1. Each of the lower reflecting mirrors 42 has a length of 10 mm along the inclination direction in an inclined state shown in FIG. 1.

Upper reflecting mirror rotating motors 43 for rotating the upper reflecting mirrors 41 around horizontal axes along the end faces of the display panel substrate 10 are respectively connected to one end of each of the upper reflecting mirrors 41. The upper reflecting mirror rotating motors 43 rotate the upper reflecting mirrors 41 by an angle of 10° to 40° with respect to the vertical direction, thus finely adjusting the direction of light reflection from each of the upper reflecting mirrors 41.

In the same way, lower reflecting mirror rotating motors 44 for rotating the lower reflecting mirrors 42 around horizontal axes along the end faces of the display panel substrate 10 are respectively connected to one end of each of the lower reflecting mirrors 42. The lower reflecting mirror rotating motors 44 rotate the lower reflecting mirrors 42 by an angle of 10° to 40° with respect to the vertical direction, thus finely adjusting the direction of light reflection in each of the lower reflecting mirror 42.

The upper reflecting mirror rotating motors 43 respectively are slid horizontally along the x-axis by upper reflecting mirror sliding cylinders 45 so that the positions of the upper reflecting mirror rotating motors 43 can be adjusted. Furthermore, the upper reflecting mirror sliding cylinders 45 can be vertically moved by upper reflecting mirror raising and lowering cylinders 46 so that the positions of the upper reflecting mirror sliding cylinders 45 can be adjusted. The upper reflecting mirror raising and lowering cylinders 46 are respectively attached to the sliding blocks 34 located above the corresponding upper reflecting mirrors 41. Therefore, each of the upper reflecting mirror raising and lowering cylinders 46 vertically moves the corresponding upper reflecting mirror 41 together with the corresponding upper reflecting mirror sliding cylinder 45.

The lower reflecting mirror rotating motors 44 are respectively slid horizontally along the x-axis by lower reflecting mirror sliding cylinders 47 so that the positions of the lower reflecting mirror rotating motors 44 can be adjusted. Furthermore, the lower reflecting mirror sliding cylinders 47 can be vertically moved by lower reflecting mirror raising and lowering cylinders 48 so that the positions of the lower reflecting mirror sliding cylinders 47 can be adjusted. The lower reflecting mirror raising and lowering cylinders 48 are respectively attached to the connection blocks 38 respectively attached to the end-face illuminating units 39 for respectively illuminating the end faces of the corresponding display panel substrate 10 with light. Therefore, each of the lower reflecting mirror raising and lowering cylinders 48 vertically moves the corresponding lower reflecting mirror 42 together with the corresponding lower reflecting mirror sliding cylinder 47.

Figure 2:
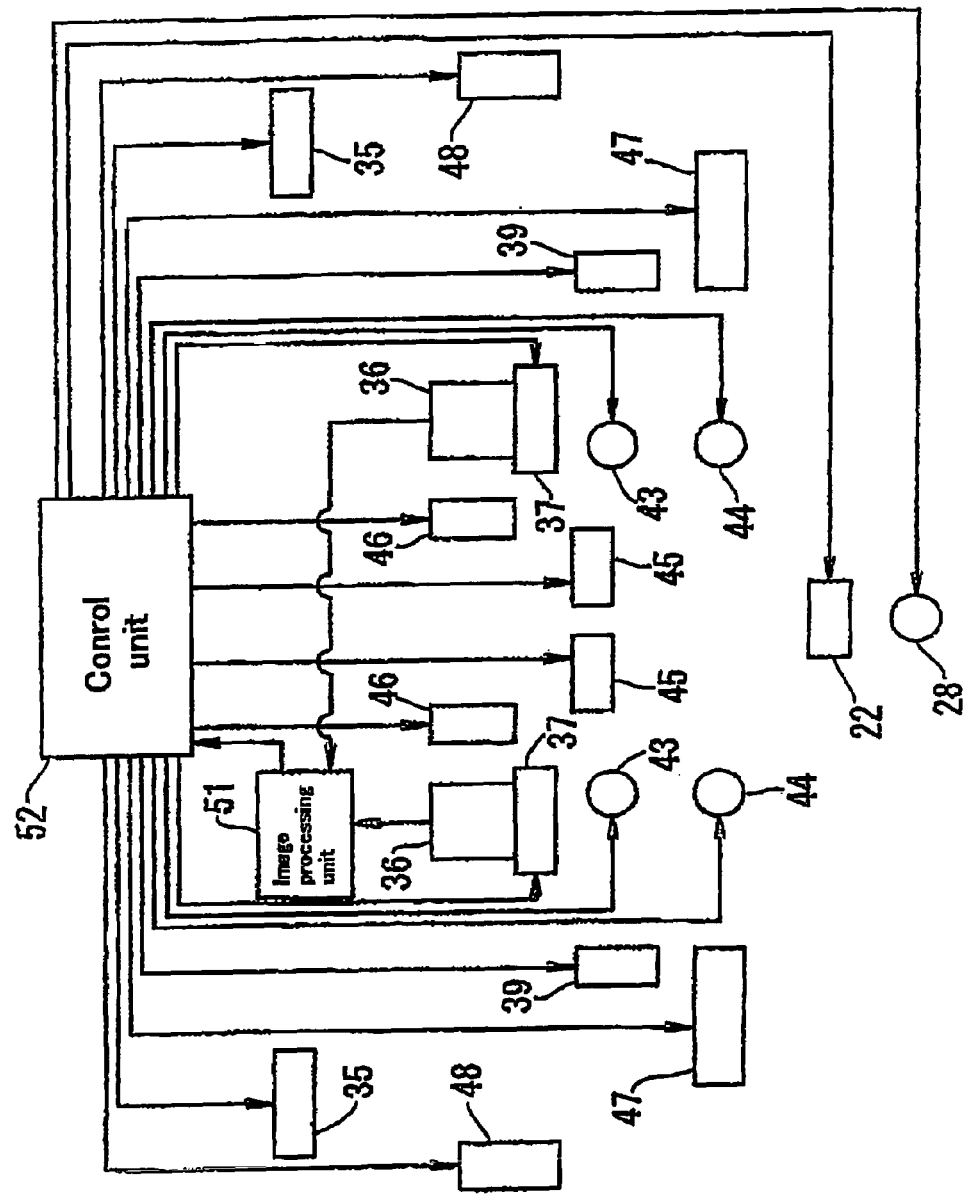
FIG. 2 is a block diagram of a control system of the inspection apparatus for inspecting an end face of a transparent substrate according to the present invention.

FIG. 2 is a block diagram of a control system of the inspection apparatus 1 for inspecting an end face of a transparent substrate according to the present invention. Image data captured by the CCD cameras 36 is input to the image processing unit 51 so that the image data captured by the CCD cameras 36 is subjected to image processing in the image processing unit 51. The output of the image processing unit 51 is output to a control unit 52. The control unit 52 respectively controls the DD motor 22, the y-axis servomotor 28, the optical system moving servomotors 35, the epi-illuminating units 37, the upper reflecting mirror rotating motors 43, the lower reflecting mirror rotating motors 44, the upper reflecting mirror sliding cylinders 45, the upper reflecting mirror raising and lowering cylinders 46, the lower reflecting mirror sliding cylinders 47, and the lower reflecting mirror raising and lowering cylinder 48.

The inspection apparatus 1 having the structure described above can simultaneously inspect each end face located at both sides of the display panel substrate 10. In the inspection apparatus 1 for inspecting an end face of a transparent substrate according to the present invention, first, the target display panel substrate 10 to be inspected is placed on the rotating table 21. The display panel substrate 10 placed on the rotating table 21 is fixed on the rotating table 21 by vacuum holding in a horizontal position so that the outer periphery of the placed display panel substrate 10 is protruded out of the circumference of the rotating table 21.

When the display panel substrate 10 is fixed on the rotating table 21, then the control unit 52 controls the y-axis servomotor 28 and the DD motor 22 to adjust the position of the rotating table 21. The rotating table 21 is adjusted so that a pair of corners of the fixed display panel substrate 10 is located within the imaging regions of the CCD cameras 36 above the rotating table 21.

In this state, the control unit 52 turns on the epi-illuminating units 37 to illuminate the imaging regions and the surroundings below the corresponding CCD cameras 36 with light. Image data of the pair of corners captured by the CCD cameras 36 to supplied to the image processing unit 51, and the image data to then subjected to image processing. Based on the results of image processing performed by the image processing unit 51, the control unit 52 drives the optical system moving servomotors 35 provided above the support 31, the y-axis servomotor 28 and the DD motor 22 to adjust the position of the rotating table 21 so that the pair of corners of the display panel substrate 10 fixed on the rotating table 21 respectively match the centers of the imaging regions of the CCD cameras 36.

When the pair of corners of the display panel substrate 10 respectively match the centers of the imaging regions of the CCD cameras 36, then the end-face illuminating units 39 integrally attached to the sliding blocks 34 with the connection blocks 38 therebetween respectively oppose the end faces of the display panel substrate 10 fixed on the rotating table 21.

In this state, the control unit 52 drives the y-axis servomotor 28 to cause the rotating table 21 supporting the display panel substrate 10 to move along the y-axis and, during this moving, the end-face illuminating units 39 are intermittently turned on at predetermined intervals. While the end-face illuminating units 39 are on, the state of each of the end faces at both sides of the display panel substrate 10 is inspected based on the images captured by the CCD cameras 36.

Figure 13:
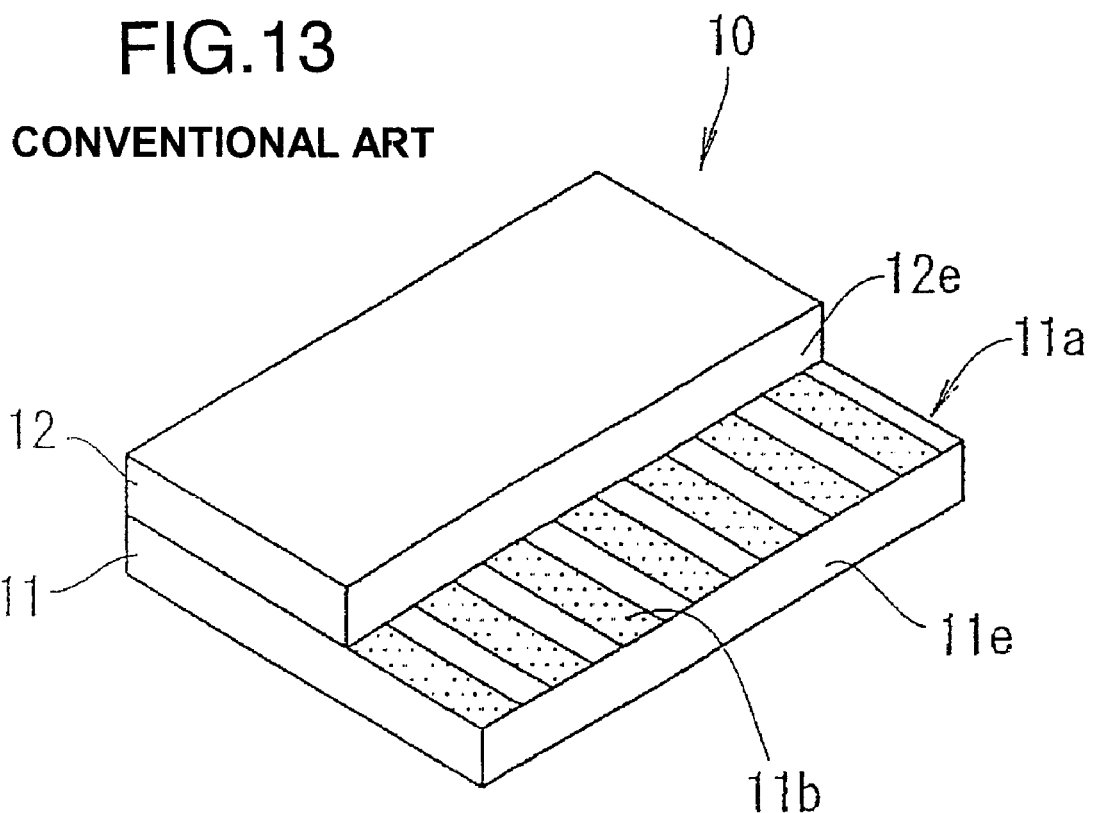
FIG. 13 is a perspective view schematically showing the structure of a display panel substrate.
Figure 14:
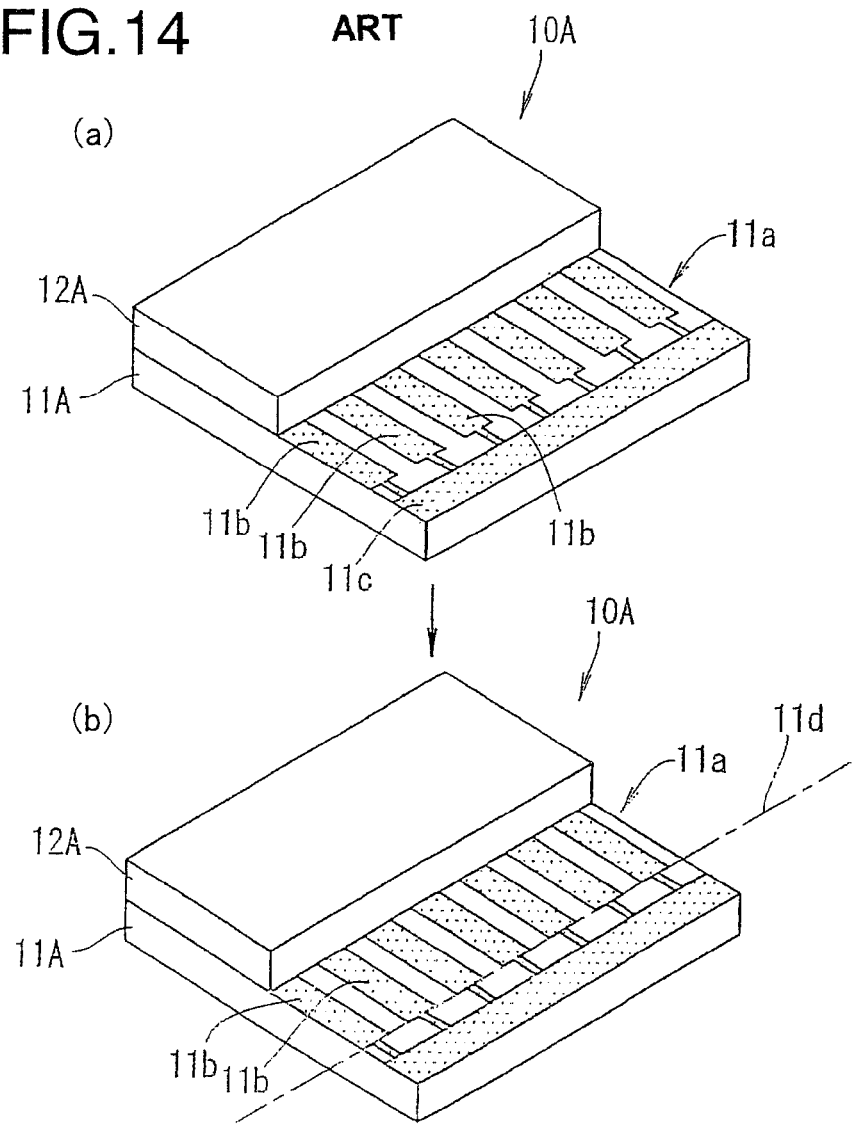
FIG. 14(a) is a schematic perspective view for showing a procedure for manufacturing the display panel substrate.
FIG. 14(b) is a schematic perspective view for showing a procedure for manufacturing the display panel substrate.
Figure 15:
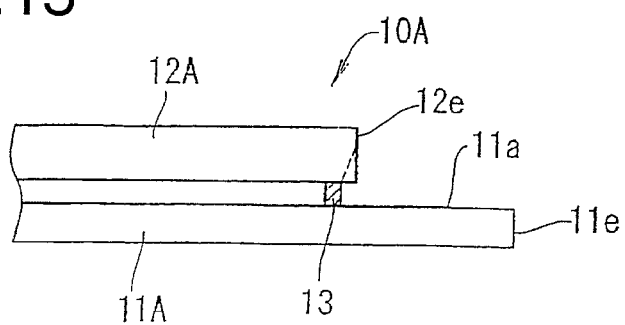
FIG. 15 is a sectional view showing the main part of the display panel substrate.

As shown in FIG. 13, the inspection apparatus 1 for inspecting an end face of a transparent substrate according to the present invention can simultaneously inspect both the end face 11e adjacent to the terminal section 11a of the TFT substrate 11 and the end face 12e of the CF substrate 12 in the display panel substrate 10 and both the other end face of the TFT substrate 11 and the other end face of the CF substrate 12 at a side edge opposite to another side end of the display panel substrate 10 where the terminal section 11a is provided.

In this case, based on the image data captured by the CCD cameras 36, the control unit 52 controls the upper reflecting mirror raising and lowering cylinders 46 respectively attached to the sliding blocks 34 and the upper reflecting mirror sliding cylinders 45 respectively attached to the upper reflecting mirror raising and lowering cylinders 46 to adjust the vertical position and the position in the y-axis direction of each of the upper reflecting mirrors 41 and the upper reflecting mirror rotating motors 43 is respectively rotated on a horizontal axis along the y-axis direction to adjust the direction of light reflection. Therefore, the light emitted from the end-face illuminating units 39 and reflected from the upper reflecting mirrors 41 is respectively illuminated on the imaging region of the CCD cameras 36 including the end faces and their vicinity at both sides of the display substrate 10.

Moreover, based on the image data captured by the CCD cameras 36, the control unit 52 drives the lower reflecting mirror raising and lowering cylinders 48 and the lower reflecting mirror sliding cylinders 47, which are respectively attached to the sliding blocks 34 with the connection blocks 38 therebetween to adjust to the vertical position and the position of the y-axis direction of each of the lower reflecting mirrors 42 and the lower reflecting mirror rotating motors 44 is respectively rotated on a horizontal axis along the y-axis direction to adjust the direction of light reflection. Therefore, the light emitted from the end-face illuminating units 39 and reflected from the lower reflecting mirrors 41 is respectively illuminated on the imaging region of the CCD cameras 36 including the end faces and their vicinity at both sides of the display substrate 10.

When each of the end-face illuminating units 39 respectively is turned on, light emitted from each of the end-face illuminating units 39 and reflected from each of the corresponding lower reflecting mirrors 42 is respectively illuminated on each end face of the display panel substrate 10. Then, the light reflected from each of the end faces is captured by the corresponding CCD cameras 36. Light that is respectively reflected from each of the upper reflecting mirrors 41 is illuminated on each of the end faces of the display panel substrate 10 and then, the light reflected from each of the end faces is captured by the corresponding CCD cameras 36.

For light that is reflected from the upper reflecting mirrors 41 and the lower reflecting mirrors 42 and then is reflected from each of the end faces of the display panel substrate 10, if no defect, such as a chipping, is present in the end faces of the display panel substrate 10, the intensity of light received by the CCD cameras 36 is constant. However, if a defect, such as a chipping, is present in the end faces, the intensity of light received by the CCD cameras 36 becomes higher due to the diffused reflection of light in the defect portion.

In the case when the terminal section of the display panel substrate 10 is inspected, the imaging region of each of the CCD cameras 36 includes both the end face lie adjacent to the terminal section 11a of the TFT substrate 11 and the end face 12e adjacent to the terminal section 11a of the CF substrate in the display panel substrate 10 and image processing to be performed by the image processing unit 51 can be switched depending on whether to choose between the case in which both the end face 11e and the end face 12e are detected and the case in which one of the end face 11e and the end face 12e is detected.

Figure 3:
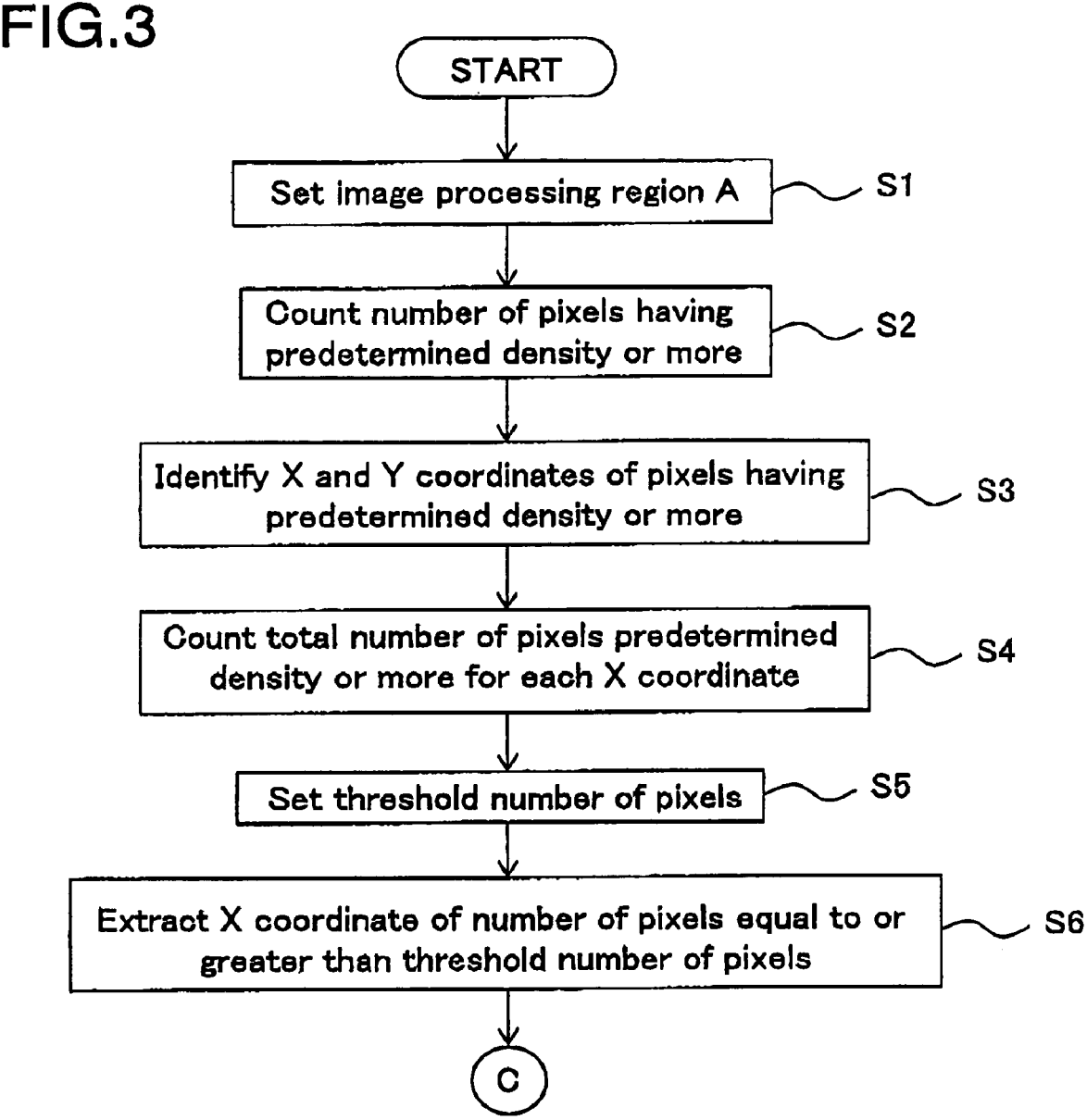
FIG. 3 is a flowchart showing an operating procedure in the inspection apparatus for inspecting an end face of a transparent substrate according to the present invention.
Figure 4:
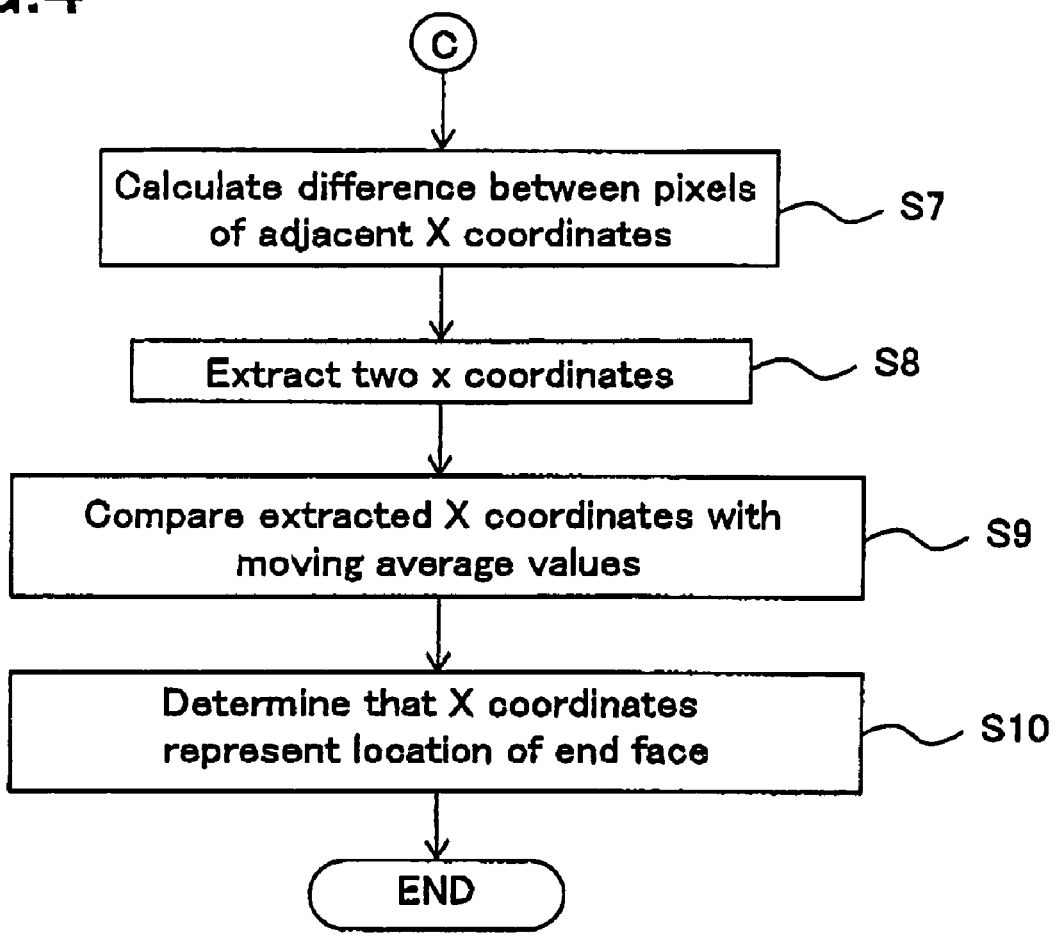
FIG. 4 is a flowchart showing an operating procedure in the inspection apparatus for inspecting an end face of a transparent substrate according to the present invention.

FIGS. 3 and 4 are a flowchart showing a procedure for image processing performed by the image processing unit 51. Since image processing of images captured by one of the CCD cameras 36 is the same as that of the other one of the CCD cameras 36, the image processing by one of the CCD cameras 36 is described below. In the flowcharts of FIGS. 3 and 4, inspecting both an end face adjacent to the terminal section 11a of the TFT substrate 11 and an end face adjacent to the terminal section 11a of the CF substrate 12 in the display panel substrate 10 is set in advance. In this case, two image processing regions A corresponding to the end faces are set as the imaging region to be captured by the one CCD camera 36 (step S1).

Figure 5:
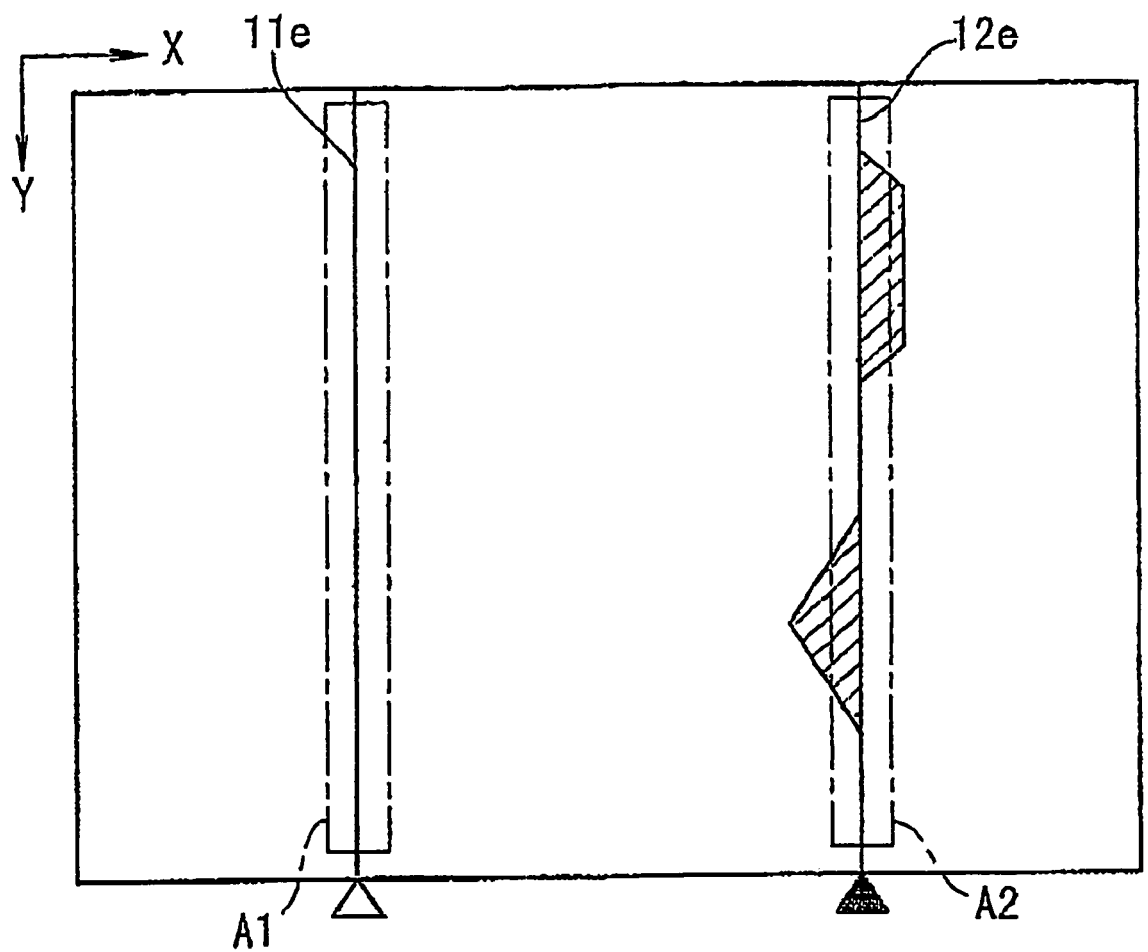
FIG. 5 is an illustration showing an example of an image for explaining the operation of the inspection apparatus for inspecting an end face of a transparent substrate according to the present invention.

FIG. 5 shows one example of an image captured by the CCD camera 36 in this case. When the end face 11e and the end face 12e adjacent to the terminal section 11a of the TFT substrate 11 in the display panel substrate 10 are respectively illuminated with light reflected from the upper reflecting mirror 41 and the lower reflecting mirror 42 by turning the end-face illuminating unit 39 on, if no defect, such as a chipping, 11a present in the end face 11e and the end face 12e, the light reflected from each of the end face 11e and the end face 12e is captured by the CCD camera 36 with a constant intensity. An area having the end face 11e as its center and a fixed width is set as an image processing region Al along the end face 11e, and an area having the end face 12e as its center and a fixed width is set as an image processing region A2 along the end face 12e.

In the case when one of the end face 11e and the end face 12e is a target for inspection instead of both the end faces 12e and 12e located at both sides of the terminal section 11a in the display panel substrate 10, the corresponding one of the image processing regions A1 and A2 is set. Hereinafter, such a set image processing region is referred to as the image processing region A.

When the image processing region A is set, as shown in FIG. 6(a), pixels that receive light whose intensity has a predetermined level or above within the set image processing region A are extracted, and the total number of extracted pixels is counted (step S2). In other words, the image density of each pixel constituting image data captured by the CCD camera 36 is determined, pixels having a predetermined density or more are extracted, and the total number of extracted pixels is counted. In FIG. 6(a), the pixels that receive light whose intensity is a predetermined level or more are filled in with black. The extraction of pixels receiving light whose intensity is a predetermined level or more is repeated every time the end-face illuminating unit 39 is intermittently turned on.

When the total number of pixels receiving light whose intensity is a predetermined level or more within the image processing region A is counted, then the x and y coordinates of each of the pixels having a predetermined density or more are identified (step 83). When the x and y coordinates of each pixel having a predetermined density or more are identified, then the number of pixels with a predetermined density or more within the image processing region A along the y-axis is counted for each x coordinate based on the identified x and y coordinates having a predetermined density or more(step S4). Then, based on the results of the counting, a histogram is created, as shown in FIG. 6(b).

When the histogram is created in this way, as shown in FIG. 7(a), an x coordinate for the highest number of pixels with a predetermined density or more along the y-axis is determined, the number of pixels with a predetermined density or more (the maximum number n of pixels) at the x coordinate is multiplied by a preset ratio (e.g., 60%). and the value is set as a threshold number of pixels (0.6 n) (step S6). Then as shown in FIG. 7(b), an x coordinate exhibiting that the number of pixels with a predetermined density or more is larger than the threshold number of pixels is extracted (step 86). In FIG. 7(b), at the three locations for x coordinates, 100, 101, and 110, the number of pixels with a predetermined density or more is larger than the threshold number of pixels.

When the x coordinates at which the number of pixels with a predetermined density or more is larger than the threshold number of pixels are extracted in this way, the absolute value of the difference (n1−n2) between the number n1, of pixels with a predetermined density or more at each of the extracted x coordinates and the number n2, of pixels at an adjacent x coordinate (X-1) is calculated (see step S7 in FIG. 4), and two x coordinates at which the calculated difference of the numbers of pixels is larger than the others are extracted. In FIG. 7(b), 100 and 110 are extracted as x coordinates (step S8). Then, each of the extracted x coordinates is set as a candidate for the coordinates at which an end face to be targeted for inspection is located. Then, the distance between the two x-coordinates, which are considered as the candidates for the location of the end face, is calculated.

The processing described above is sequentially performed every time the end-face illuminating unit 39 is turned on at predetermined intervals. When the x coordinates considered as the candidates for the end face to be targeted for inspection and the distance between the two x coordinates considered as the candidates are sequentially calculated every time the end-face illuminating unit 39 is turned on, then the results of the calculation are respectively compared with each sequentially obtained average values (moving average values) (step S9).

If the x coordinates considered as the candidates for the end face to be targeted for inspection and the distance between the two x coordinates considered as the candidates are respectively within a preset range with respect to the moving average values and the difference between a calculated x coordinate considered as the candidates for the end face to be targeted for inspected and the immediately previously calculated x coordinate considered as the candidates is in a preset range when these two are compared, the obtained x coordinates are determined to represent the location of the end face to be targeted for inspection (step S10).

If the x coordinates considered as the candidates for the end face to be targeted for inspection and the distance between the two x coordinates considered as the candidates are not within the preset range with respect to the moving average values, it is determined that a defect, such as a chipping, has occurred in the end face and its effect is present in an image. Therefore, the obtained x coordinates are not employed as the location of the end face, and a defeat inspection is performed using the mean value of the x coordinates that have already been obtained or the location of the end face determined at the previous inspection.

Figure 8:
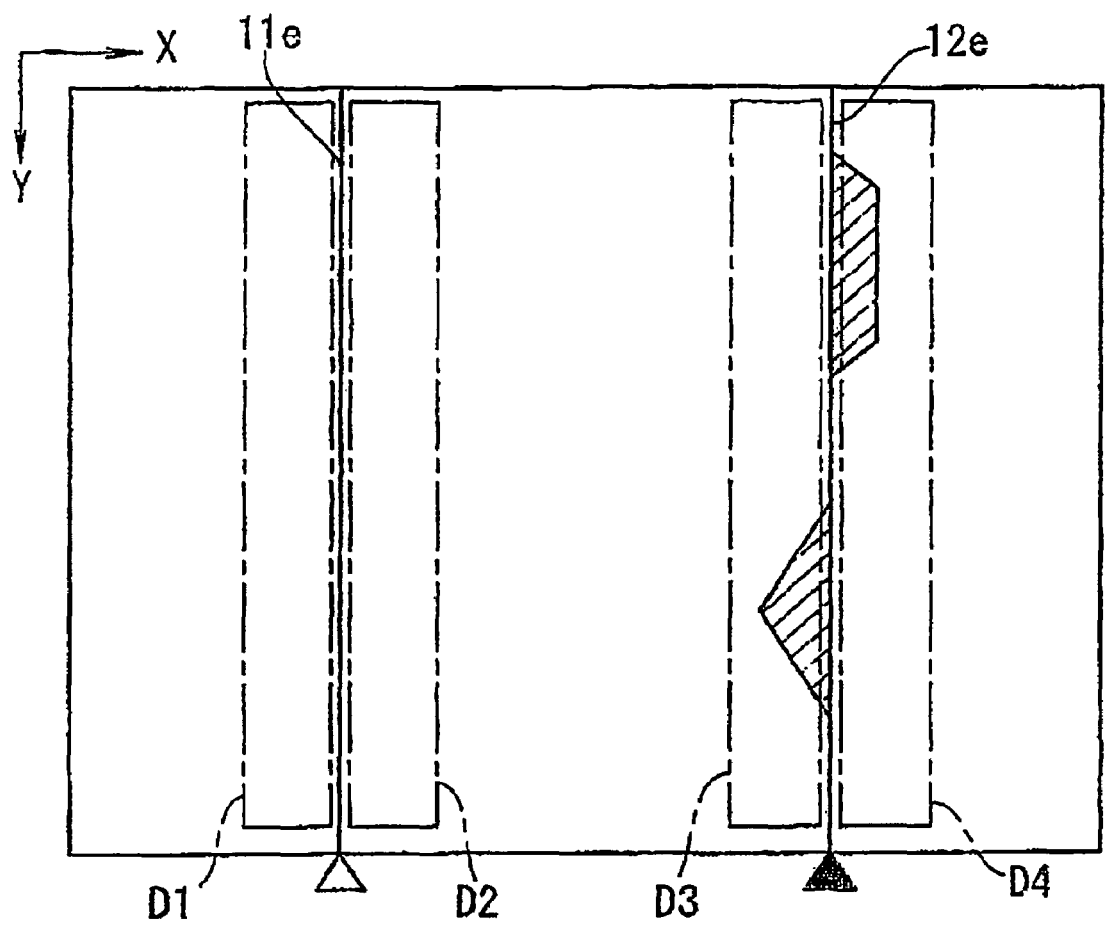
FIG. 8 is an illustration showing an image for explaining the image processing in the inspection apparatus for inspecting an end face of a transparent substrate according to the present invention.

When the x coordinates are identified and the identified x coordinates are determined to represent the location of the end face to be targeted for inspection in this way, then a defect inspection is performed. In this case, as shown in FIG. 8, for example, with respect to the set end face, first, a defect inspection region is set. FIG. 8 shows the case in which the end face 11e adjacent to the terminal section 11a of the TFT substrate 11 and the end face 12e of the CF substrate 12, in the display panel substrate 10 are both targeted for inspection. In this case, defect inspection regions D1 to D4 are set respectively along both sides of the set end faces.

The defect inspection region D1 set outside the end face 11e of the TFT substrate 11 is set in order to detect a convex defect portion protruding from the end face 11e of the TFT substrate 11. The defect inspection region D2 set inside the end face 11e of the TFT substrate 11 is set in order to detect a concave defect portion for the end face 11e of the TFT substrate 11. Similarly, the defect inspection region D3 set outside the end face 12e of the CF substrate 12 is set in order to detect a convex defect portion protruding from the end face 12c of the CF substrate 12. The defect inspection region D4 set inside the end face 12e of the CF substrate 12 is set in order to detect a concave defect portion for the end face 12e of the CF substrate 12.

These defect inspection regions are not limited to the configuration respectively setting defect inspection regions at both sides of each of the end faces. For example, if inspecting a concave defect portion is not necessary, as in the case in which the end face 11e of the TFT substrate 11 is subjected to chamfering, it is unnecessary to set the defect inspection region D2 inside the end face 11e of the TFT substrate 11. Furthermore, defect inspection regions are not limited to the configuration respectively setting defect inspection regions at both sides of each of the end faces and one defect inspection region for each end face may be set so that the end face is located in the center of the defect inspection region.

Figure 9:
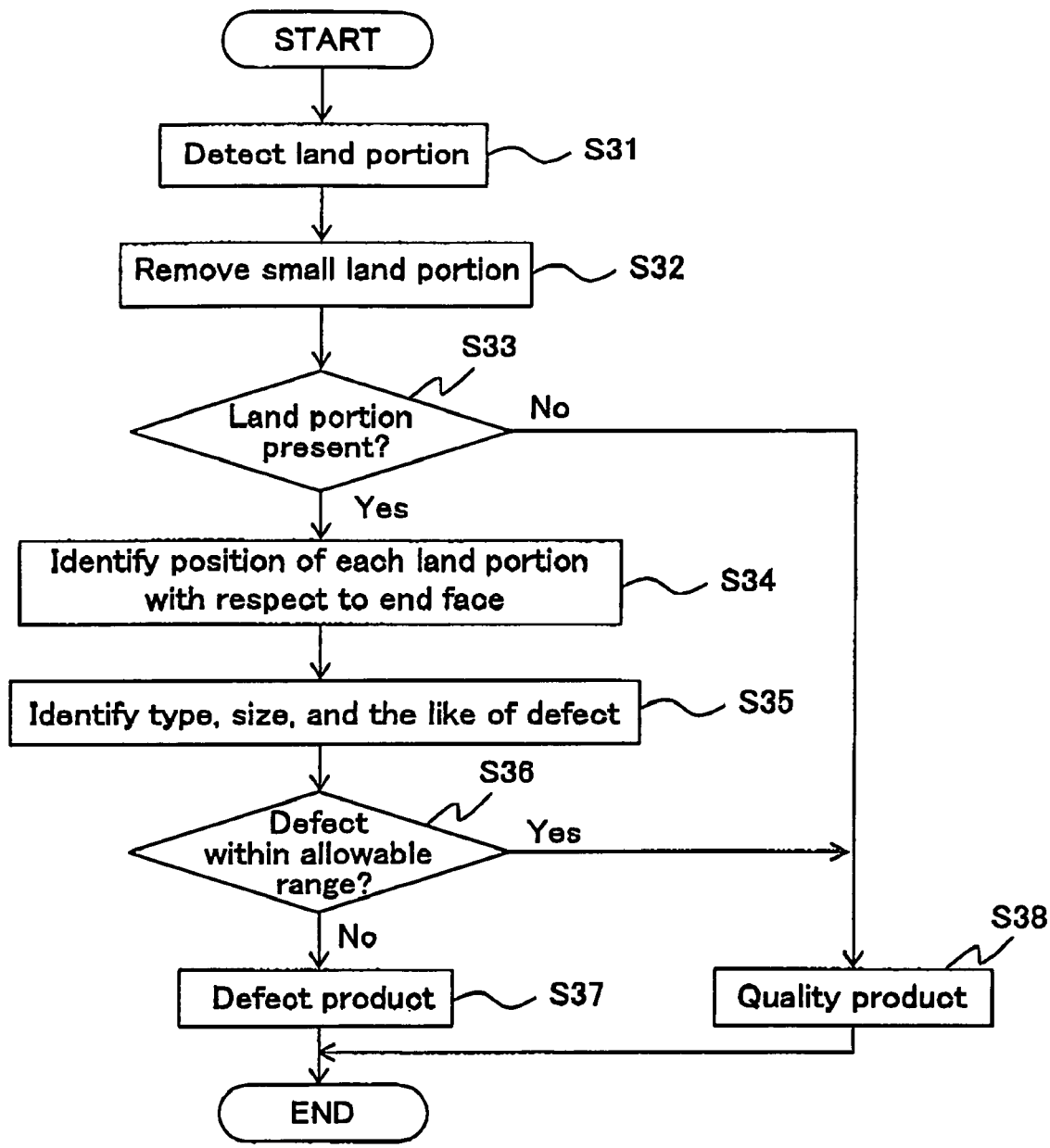
FIG. 9 is a flowchart showing an image processing procedure in the inspection apparatus for inspecting an end face of a transparent substrate according to the present invention.

When the defect inspection regions are set in this way, then a defect inspection processing for each end face is performed. FIG. 9 is a flowchart showing a procedure for the defect inspection. In this defect inspecting processing, every time each end-face illuminating unit 39 is turned on at predetermined intervals, it is inspected whether an island that has a high density (referred to as land portion) is present in the set defect inspection regions. Then, for every defect inspection region, the total number of land portions, the area of each land portion, and the maximum value and the minimum value of the X coordinates and the maximum value and the minimum value of the y coordinates in each land portion are calculated (see stop S31 in FIG. 9, and the same applies to below).

In this case, when a land portion whose area in each defect inspection region is smaller than a preset threshold, the land portion is not identified as a target land portion. Therefore, such a small land portion is determined not to be targeted for the subsequent processing (step S32).

In the case in which a land portion having a predetermined size or more is present in each defect-inspection region (step 833), when the presence of the land portion is detected in each defect inspection region, then the distance between the land portion and the end face is calculated (step 834). FIGS. 10(*a*) to (*a*) show the locational relationships between the end face 11*e* of the TFT substrate 11 and land portions L detected in the defect inspection regions D1 and D2 located at the both sides of the end face 11*e*. As shown in FIG. 10, the relationship between the end face 11*e* and each land portion L is calculated based on the maximum value and minimum value of the x coordinates in the land portion and the x coordinate of the end face 11*e*.

FIGS. 10(*a*) and 10(*c*) show the case in which the x coordinate of the end face 11*e* is located between the maximum value and the minimum value of the x coordinates in the land portion L. FIG. 10(*b*) shows the case in which both the maximum value and the minimum value of the x coordinates in the land portion L are larger than the x coordinate of the end face 11*e*. In each case, the distance LA between the maximum value of the x coordinates in the land portion L and the end face 11*e* and the distance LB between the minimum value of the x coordinates in the land portion L and the end face 11*e* are calculated. Then, the location of the land portion L with respect to the end face 11*e* is identified from each calculated distance LA and LB and the relationships between the x coordinate of the end face 11*e* and the maximum value and minimum value of the x coordinates in the land portion L.

When the locational relationships between each land portion and the end face are identified in this way, then the type of each defect, i.e., a concave defeat or a convex defect, is identified for each land portion based on the defect inspection region in which each land portion is detected. Furthermore, the size of each defect is identified based on the area of each land portion, and the depth of a concave defect or the amount of protrusion of a convex defect is identified based on the distance between each land portion and the end face (step 35).

Thereafter, based on the type, the size, and the depth or the amount of protrusion of the existing defect, it is determined whether the defect is within an allowable range, i.e., whether the detected defect is allowable by comparing the size preset for the type of the defect with the depth or the amount of protrusion (step S36). If the existing defect is not within the allowable range, the target display panel substrate 10 to be inspected is determined to be a defective product (step S37). If the existing defect is within the allowable range, the target display panel substrate 10 to be inspected is determined to be a quality product (step S38).

When the inspection for the pair of end faces corresponding to two sides of the display panel substrate 10 is completed in this way, then the rotating table 21 on which the display panel substrate 10 is placed and fixed is moved in order to return to the starting position and is rotated by 90° around the vertical axis by the DD motor 21, and each sliding block 34 is moved based on data of, for example, the size of the display panel substrate 10. Thereafter, inspection for the pair of end faces corresponding to the remaining two sides of the display panel substrate 10 is performed by the same inspection method as that described above.

For the inspection for end faces corresponding to the four Bides of the display panel substrate 10, two inspection apparatuses may be used in order to reduce the time required for inspection instead of using one inspection apparatus for inspecting an end face of a transparent substrate according to the present invention as described above.

Illuminating the end faces with a light emitted from the epi-illuminating unit 37 being turned on intermittently while the end-face illuminating unit 39, which is turned on at predetermined intervals during inspection of end faces, is off as shown in FIG. 11, detecting an intensity of the reflected light with the CCD camera 36, and performing an inspection for the end faces of the transparent substrate by the same method as the image processing method described above increase the directions of lights illuminated on the end faces of the display panel substrate. This improves the accuracy of detecting defects occurred in the end faces of the display panel substrate, such as a chipping, a hollow, and the like.

For the inspection for end faces of the display panel substrate 10, due to the reason that defects that are easy to be detected by the epi-illuminating unit 37 are different from those by the end-face illuminating unit 39 and that defects occurring vary depending on the material used in the glass substrate, an inspection that uses both the epi-illuminating unit 37 and the end-face illuminating unit 39 or an inspection that uses one of the epi-illuminating unit 37 and the end-face illuminating unit 39 can be selected.

Since the contrast of images obtained by illuminating the end face of the display panel substrate 10 with the light emitted from the end-face illuminating unit 39 is the inverse of that of images obtained by illuminating the end face of the display panel substrate 10 with the light emitted from the epi-illuminating unit 37, the image processing procedures for both illuminating are slightly different from each other.

Furthermore, in general, after the gap between the TFT substrate 11 and the CF substrate 12 is filled with liquid crystals, each edge of the end faces of the TFT substrate 11 and the CF substrate 12 is, for example, subjected to chamfering by wet grinding with grind stones or illuminating each edge of the end faces with a laser beam. In particular, in the case in which the short link described above is removed and the edge of the terminal section 11*a* is subjected to chamfering, it is necessary to check whether the edge is reliably subjected to chamfering by a predetermined amount in order to fully remove the short link and to increase the strength of each edge.

Figure 12:
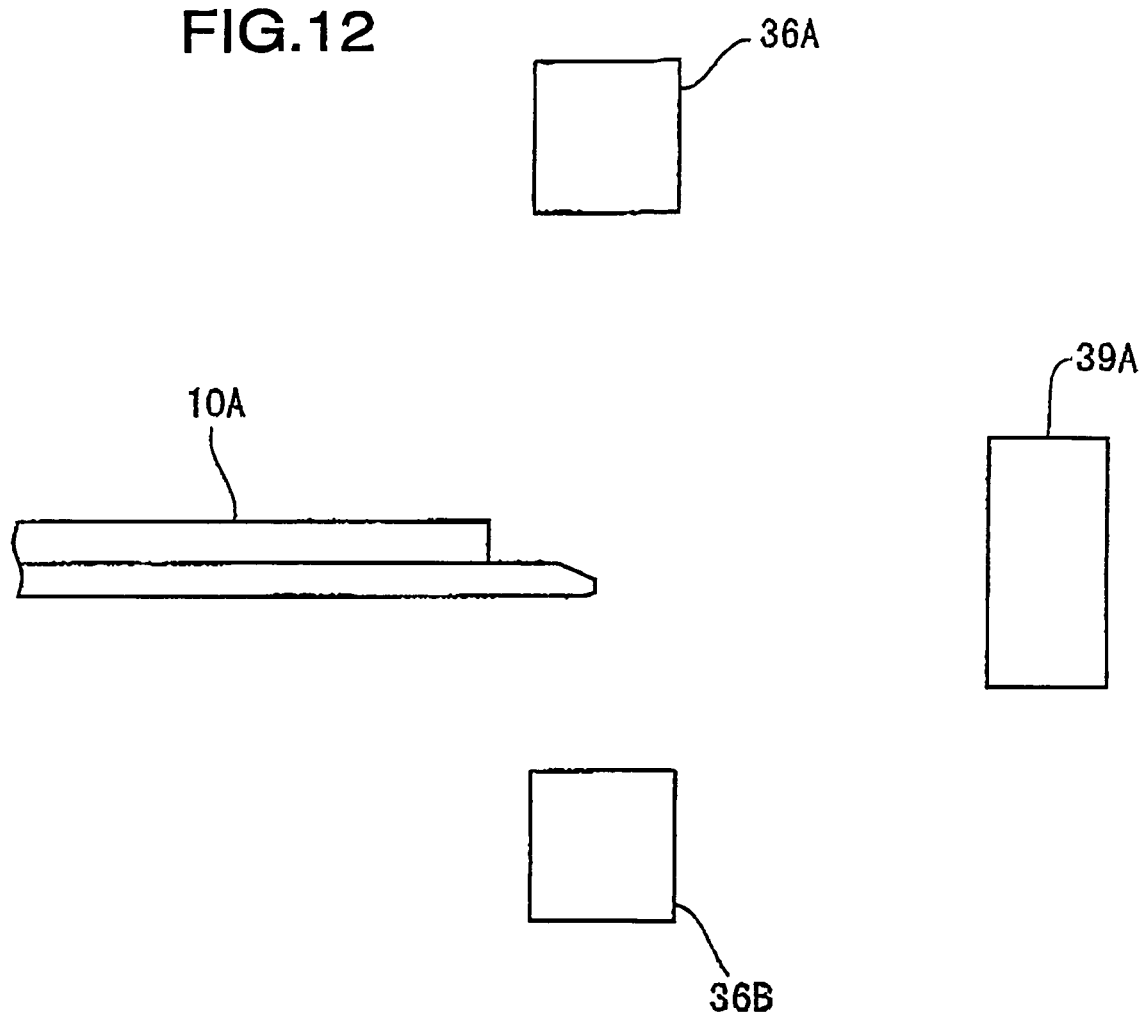
FIG. 12 is a schematic diagram showing the structure of an optical system of the inspection apparatus for inspecting an end face of a transparent substrate.

FIG. 12 is a schematic diagram showing the structure of an optical system of the inspection apparatus for inspecting an end face of a transparent substrate for inspecting the amount of chamfering after each edge of the end face of the display panel substrate 10 is subjected to chamfering. In FIG. 12, the epi-illuminating units, the upper reflecting mirrors, the lower reflecting mirrors, the driving mechanism for adjusting the position and the angle of each of the upper reflecting mirrors and the lower reflecting mirrors are omitted from FIG. 1 and a lower CCD camera 36B is added.

For the inspection for the amount of chamfering using this inspection apparatus, an end face of the bonded glass substrate 10A is illuminated with a light emitted from an end-face illuminating unit 39A, an image of the end face is captured by an upper CCD camera 36A and the lower CCD camera 36B, and it is checked whether the amount of chamfering for which the inspection 18 performed by the same image processing method as that described above is appropriate.

As such, in the inspection apparatus for inspecting an end face of a transparent substrate according to the present invention, since each side edge to be targeted for inspection the display panel substrate 10 placed on the rotating table 21 is respectively protruded into a side of the rotating table 21 and the light emitted from each of the end-face illuminating units 39 is reflected from each of the lower reflecting mirrors 42 provided below the display panel substrate 10 to illuminate each end face of the display panel substrate 10, each end face of the display panel substrate 10 is reliably illuminated with a light.

Since an image of each end face and its adjacent area of the display panel substrate 10 illuminated with a light is captured by each of the CCD cameras 36 provided above the display panel substrate 10 and defects of each end face are detected based on the intensity of light received by each of the CCD cameras 36, the defects can be detected precisely and reliably. Furthermore, the type, the location, the size and the like of each defect can be detected.

For example, in a case with a method where an end face is illuminated with light and defects are detected based on an image pattern of the end face, the image pattern can not be correctly recognized and thus the defects may not be correctly detected due to the presence of the terminal section 11a adjacent to each end face of the display panel substrate 10 illuminated with a light. In contrast to this, the inspection apparatus for inspecting an end face of a transparent substrate according to the present invention does not cause this problem.

Since each of the end-face illuminating units 39 for respectively illuminating the each end face of the display panel substrate 10 with light is intermittently turned on, the variations in intensity of light with which each end face is illuminated can be suppressed, and furthermore, the end-face illuminating units 39 can be used with stability for the long term.

The inspection apparatus and the inspection method for inspecting an end face of a transparent substrate according to the present invention are, for example, applicable to inspection for end faces of liquid crystal display panels, which is one type of flat panel displays, organic electroluminescent (EL) displays, inorganic EL displays, plasma display panels (PDPs), and the like. The inspection apparatus and the method are also effectively applicable to inspection for end faces of transmissive-projector substrates and the like for which quartz substrates are bonded.

Furthermore, the target for inspection by the inspection apparatus for inspecting an end face of a transparent substrate according to the present invention is not limited to a bonded glass substrate, such as the display panel substrate 10. The inspection apparatus according to the present invention is applicable to inspection for an end face of a single transparent substrate, such as a single glass substrate, a single plastic substrate, or the like.

INDUSTRIAL APPLICABILITY

According to the present invention, the inspection apparatus and the inspection method for inspecting an end face of a transparent substrate are capable of precisely and reliably detecting defects in the end face of the transparent substrate using a simple and inexpensive optical system and image processing device and capable of accurately detecting the amount of chamfering of each edge of the end face of the transparent substrate after the edge is subjected to chamfering.

The invention claimed is:

1. An inspection apparatus for inspecting an end face of a transparent substrate, the apparatus comprising:
    a first illuminating means for emitting a light;
    a first reflecting means for reflecting the emitted light to the end face of the transparent substrate at a first face of the transparent substrate;
    a second reflecting means for reflecting the emitted light to the end face of the transparent substrate at a second face opposite to the first face of the transparent substrate;
    an imaging means for receiving the light reflected from the end face of the transparent substrate at at least one of the first face and the second face of the transparent substrate; and
    a detecting means for detecting a defect occurred in the end face of the transparent substrate based on an intensity of the received light.

2. An inspection apparatus according to claim 1, further comprising a table for supporting the transparent substrate in a horizontal position,
    wherein the first reflecting means, the imaging means and the second reflecting means are provided on one of the first face and the second face of the transparent substrate.

3. An inspection apparatus according to claim 2, wherein the first reflecting means, the second reflecting means and the imaging means are movable in an integral manner with respect to the table.

4. An inspection apparatus according to claim 3, wherein the first reflecting means and the second reflecting means are integrally movable with respect to the first illuminating means.

5. An inspection apparatus according to claim 4, wherein, in each of the first reflecting means and the second reflecting means, the direction that reflects the emitted is adjustable.

6. An inspection apparatus according to claim 1 or claim 2, wherein the first illuminating means intermittently emits the light to the end face of the transparent substrate and,
    the apparatus further comprises a second illuminating means for intermittently emitting a light to the end face of the transparent substrate while the first illuminating means is off.

7. An inspection apparatus according to claim 2, wherein the first illuminating means, the first reflecting means and the second reflecting means are respectively provided on the end faces at both side edges of the transparent substrate.

8. An inspection apparatus according to claim 1, further comprising a table for supporting the transparent substrate in a horizontal position, wherein the table is movable in a horizontal direction.

9. An inspection apparatus according to claim 8, wherein the table is rotatable around an axis vertical to a surface of the table.

10. An inspection apparatus according to claim 1, wherein the first illuminating means is a linear light source extending parallel to the end face of the transparent substrate.

11. An inspection apparatus according to claim 10, wherein the linear light source is an LED array.

12. An inspection apparatus according to claim 1, wherein the imaging means is a CCD camera.

13. An inspection apparatus according to claim 1, wherein the detecting means determines an image density of each pixel in image data captured by the imaging means and identifies the end face of the transparent substrate based on the image density of each pixel.

14. An inspection apparatus according to claim 13, wherein the detecting means detects a defect based on the identified end face of the transparent substrate and the image density of each pixel.

15. An inspection apparatus according to claim 1, wherein an edge of the end face is subjected to chamfering.

16. An inspection apparatus according to claim 1, wherein the detecting means detects diffused reflection at the end face of the transparent substrate as a defective portion having a high intensity of light.

17. An inspection apparatus according to claim 1, wherein the transparent substrate is a bonded glass substrate for which two glass substrates are bonded so that a terminal section is exposed, the two glass substrates having a predetermined gap to be filled with liquid crystals therebetween.

18. An inspection apparatus according to any one of claims 1, 2, 8 to 5, 10, to 7, 13 to 17, wherein the detecting means is capable of switching a target for inspection between one of the end faces of a bonded glass substrate or both the end faces of the bonded glass substrate, the bonded glass substrate being bonded so that a terminal section is exposed.

19. An inspection method for inspecting an end face of a transparent substrate, the inspection method comprising:
a first illuminating step of emitting a light;
a first reflecting step of reflecting the emitted light to the end face of the transparent substrate at a first face of the transparent substrate;
a second reflecting step of reflecting the emitted light to the end face of the transparent substrate at a second face opposite to the first face of the transparent substrate;
an imaging step of receiving the light reflected from the end face of the transparent substrate at at least one of the first face and the second face of the transparent substrate; and
a detecting step of detecting a defect occurred in the end face of the transparent substrate based on an intensity of the received light.

20. An inspection method according to claim 19, wherein the first illuminating step includes a step of intermittently emitting the light.

21. An inspection method according to claim 19 or claim 20, further including a second illuminating step of intermittently emitting a light while the light emitted in the first illuminating step is off.

22. An inspection method according to any one of claims 19 to 20, wherein the detecting step determines an image density of each pixel in image data captured by the imaging step, identifies the end face of the transparent substrate based on the image density and detects a defect based on the identified end face of the transparent substrate and the image density of each pixel.

23. An inspection method according to claim 19, wherein an edge of the end face is subjected to chamfering.

24. An inspection method according to claim 19, wherein the detecting step detects diffused reflection at the end face of the transparent substrate as a defective portion having a high intensity of light.

25. An inspection method according to claim 19, wherein the transparent substrate is a bonded glass substrate for which two glass substrates are bonded so that a terminal section is exposed, the two glass substrates having a predetermined gap to be filled with liquid crystals therebetween.

26. An inspection method according to any one of claims 19, 20 or 23 to 25, wherein the detecting step is capable of switching an inspecting target between one of the end faces of a bonded glass substrate or both the end faces of the bonded glass substrate, the bonded glass substrate being bonded so that a terminal section is exposed.

27. An inspection apparatus according to claim 1, wherein the first illuminating means intermittently emits the light.

28. An inspection apparatus according to claim 1, wherein the detecting means detects the defect occurred in the end face of the transparent substrate based on an image density corresponding to the intensity of the received light.

29. An inspection method according to claim 19, wherein the first illuminating step includes a step of intermittently emitting the light.

30. An inspection method according to claim 19, wherein the detecting step includes a step of detecting the defect occurred in the end face of the transparent substrate based on an image density corresponding to the intensity of the received light.

* * * * *